United States Patent
Egloff et al.

(10) Patent No.: US 11,253,652 B2
(45) Date of Patent: Feb. 22, 2022

(54) DEVICE FOR DISPENSING A SUBSTANCE

(71) Applicant: SHL Medical AG, Zug (CH)

(72) Inventors: Christoph Egloff, Löhningen (CH);
Ludwig Daniel Weibel, Waldstatt (CH)

(73) Assignee: SHL MEDICAL AG, Zug (CH)

( * ) Notice: Subject to any disclaimer, the term of this patent is extended or adjusted under 35 U.S.C. 154(b) by 261 days.

(21) Appl. No.: 16/462,278

(22) PCT Filed: Nov. 27, 2017

(86) PCT No.: PCT/EP2017/080535
§ 371 (c)(1),
(2) Date: May 20, 2019

(87) PCT Pub. No.: WO2018/096149
PCT Pub. Date: May 31, 2018

(65) Prior Publication Data
US 2019/0351143 A1    Nov. 21, 2019

(30) Foreign Application Priority Data
Nov. 28, 2016  (EP) .................................... 16200929

(51) Int. Cl.
*A61M 5/24* (2006.01)
*A61M 5/19* (2006.01)
*A61M 5/20* (2006.01)

(52) U.S. Cl.
CPC ............ *A61M 5/2448* (2013.01); *A61M 5/19* (2013.01); *A61M 5/2066* (2013.01);
(Continued)

(58) Field of Classification Search
CPC ........... A61M 2005/14252; A61M 2005/1585; A61M 5/19; A61M 5/1409; A61M 5/2066; A61M 5/2448
See application file for complete search history.

(56) References Cited

U.S. PATENT DOCUMENTS 3,451,393 A    6/1969  Sarnoff
4,689,042 A    8/1987  Sarnoff et al.
(Continued)

FOREIGN PATENT DOCUMENTS

AU    2010207762 A1    9/2010
CH         700473 A1    8/2010
(Continued)

OTHER PUBLICATIONS

International Search Report Corresponding to PCT/EP2017/080535 dated Jan. 2, 2018.
(Continued)

*Primary Examiner* — Emily L Schmidt
(74) *Attorney, Agent, or Firm* — McDonnell Boehnen Hulbert & Berghoff LLP

(57) ABSTRACT

A device (1) for dispensing a substance to a patient comprising a cylindrical first container (2) containing the substance and a second container (3) containing a liquid. The device further comprises an injection device (4) and transfer mechanism (5) for transferring the liquid from the second container (3) to the first container (2) and from the first container (2) to the injection device (4). The first container (2) has a connection element (7) and a plunger (9) that can be moved between the first (6) and second ends (8). By moving the plunger (9) towards the first end (6), liquid contained therein can be dispensed via the injection device (4). The injection device (4) comprises a piercing cannula (15) and an indwelling cannula (16). In an initial position, a distal end region of the piercing cannula (15) extends coaxially in the interior of the indwelling cannula (16).

14 Claims, 9 Drawing Sheets

(52) U.S. Cl.
CPC ........ *A61M 5/2422* (2013.01); *A61M 5/2466* (2013.01); *A61M 2005/202* (2013.01); *A61M 2005/206* (2013.01); *A61M 2005/2073* (2013.01); *A61M 2005/2086* (2013.01); *A61M 2005/247* (2013.01)

(56) References Cited

U.S. PATENT DOCUMENTS

| | | | |
|---|---|---|---|
| 5,267,963 A | 12/1993 | Bachynsky | |
| 5,876,380 A | 3/1999 | Manganini et al. | |
| 5,931,814 A | 8/1999 | Alex et al. | |
| 6,277,091 B1 | 8/2001 | Genet | |
| 6,290,680 B1 | 9/2001 | Forsberg et al. | |
| 6,659,978 B1 | 12/2003 | Kasuga et al. | |
| 6,679,248 B2 | 1/2004 | Stadelhofer | |
| 6,699,218 B2 | 3/2004 | Flaherty et al. | |
| 6,902,543 B1 | 6/2005 | Cherif-Cheikh et al. | |
| 6,960,192 B1 | 11/2005 | Flaherty et al. | |
| 7,470,253 B2 | 12/2008 | Kriesel et al. | |
| 7,837,653 B2 | 11/2010 | Kriesel et al. | |
| 7,981,076 B2 | 7/2011 | Sullivan et al. | |
| 8,728,054 B2 | 5/2014 | Schulhof | |
| 9,022,995 B2 | 5/2015 | Schulhof et al. | |
| 9,138,534 B2 | 9/2015 | Yodfat et al. | |
| 9,566,384 B2 | 2/2017 | Gyrn et al. | |
| 2001/0025168 A1 | 9/2001 | Gross et al. | |
| 2003/0036725 A1 | 2/2003 | Lavi et al. | |
| 2003/0135159 A1 | 7/2003 | Daily et al. | |
| 2004/0010207 A1 | 1/2004 | Flaherty et al. | |
| 2004/0049129 A1 | 3/2004 | Qi | |
| 2007/0060875 A1 | 3/2007 | Bassarab et al. | |
| 2007/0060876 A1 | 3/2007 | Bassarab et al. | |
| 2007/0060877 A1 | 3/2007 | Bassarab et al. | |
| 2007/0129673 A1 | 6/2007 | Bassarab et al. | |
| 2008/0215006 A1 | 9/2008 | Thorkild | |
| 2008/0228144 A1 | 9/2008 | Liniger et al. | |
| 2009/0043278 A1 | 2/2009 | Tanaka et al. | |
| 2009/0093792 A1 | 4/2009 | Gross et al. | |
| 2009/0105646 A1 | 4/2009 | Hendrixson et al. | |
| 2009/0131864 A1 | 5/2009 | Pickhard | |
| 2009/0204077 A1 | 8/2009 | Hasted et al. | |
| 2009/0292245 A1 | 11/2009 | Basso et al. | |
| 2010/0087799 A1 | 4/2010 | Galbraith et al. | |
| 2010/0130931 A1 | 5/2010 | Yodfat et al. | |
| 2010/0262074 A1 | 10/2010 | Seiferlein et al. | |
| 2010/0274186 A1 | 10/2010 | Seiferlein et al. | |
| 2011/0034883 A1 | 2/2011 | Gyrn et al. | |
| 2011/0036844 A1 | 2/2011 | Gyrn et al. | |
| 2011/0040263 A1 | 2/2011 | Herdum et al. | |
| 2011/0043357 A1 | 2/2011 | Peatfield et al. | |
| 2011/0046456 A1 | 2/2011 | Hordum et al. | |
| 2011/0060274 A1 | 3/2011 | Kuhn | |
| 2011/0073620 A1 | 3/2011 | Verrilli | |
| 2011/0077588 A1 | 3/2011 | Hirschel et al. | |
| 2011/0098652 A1 | 4/2011 | Hasted et al. | |
| 2011/0130723 A1 | 6/2011 | Hirschel et al. | |
| 2011/0301534 A1 | 12/2011 | Renz et al. | |
| 2013/0338592 A1 | 12/2013 | Calasso | |
| 2014/0058360 A1 | 2/2014 | Schoonmaker et al. | |
| 2014/0074062 A1* | 3/2014 | Caffey | A61M 5/1452 604/506 |
| 2014/0114240 A1 | 4/2014 | Joedicke et al. | |
| 2014/0158700 A1 | 6/2014 | Glocker et al. | |
| 2014/0188050 A1* | 7/2014 | Dittrich | A61M 5/19 604/191 |
| 2014/0316378 A1 | 10/2014 | Magnenat et al. | |
| 2014/0332559 A1 | 11/2014 | Ritzenhoff et al. | |
| 2014/0334252 A1 | 11/2014 | Harand et al. | |
| 2014/0339112 A1 | 11/2014 | Jew et al. | |
| 2015/0196719 A1 | 7/2015 | Uchiyama | |
| 2015/0209518 A1 | 7/2015 | Moser et al. | |
| 2015/0290389 A1 | 10/2015 | Nessel | |
| 2016/0121043 A1 | 5/2016 | Weibel | |
| 2016/0213851 A1 | 7/2016 | Weibel et al. | |
| 2017/0246386 A1 | 8/2017 | Gyrn et al. | |
| 2017/0281868 A1 | 10/2017 | Roedle et al. | |
| 2017/0304525 A1 | 10/2017 | Roedle | |

FOREIGN PATENT DOCUMENTS

| | | |
|---|---|---|
| CN | 101687075 A | 3/2010 |
| EP | 3 003 426 A1 | 4/2016 |
| FR | 2799643 B1 | 4/2001 |
| GN | 101939033 A | 1/2011 |
| JP | S62-502876 A | 11/1987 |
| JP | 2011-510774 A | 4/2011 |
| JP | 2013-508054 A | 3/2013 |
| JP | 2014-519899 A | 8/2014 |
| JP | 2014-521443 A | 8/2014 |
| WO | 86/06967 A1 | 12/1986 |
| WO | 8606967 A1 | 12/1986 |
| WO | 3523576 A1 | 9/1995 |
| WO | 9915215 A1 | 4/1999 |
| WO | 0126718 A1 | 4/2001 |
| WO | 0172354 A2 | 10/2001 |
| WO | 0202165 A2 | 1/2002 |
| WO | 02/24259 A2 | 3/2002 |
| WO | 0224259 A2 | 3/2002 |
| WO | 0240083 A2 | 5/2002 |
| WO | 03090509 A2 | 11/2003 |
| WO | 2004058327 A2 | 7/2004 |
| WO | 2004089448 A1 | 10/2004 |
| WO | 2006/031500 A2 | 3/2006 |
| WO | 2006031500 A2 | 3/2006 |
| WO | 2006045132 A2 | 5/2006 |
| WO | 2006057636 A1 | 6/2006 |
| WO | 2007020237 A1 | 2/2007 |
| WO | 2007020238 A2 | 2/2007 |
| WO | 2007020239 A1 | 2/2007 |
| WO | 2007020240 A1 | 2/2007 |
| WO | 2008040478 A1 | 4/2008 |
| WO | 2008063439 A2 | 5/2008 |
| WO | 2008107378 A1 | 9/2008 |
| WO | 2008122360 A2 | 10/2008 |
| WO | 2008150715 A1 | 12/2008 |
| WO | 2008151736 A1 | 12/2008 |
| WO | 2008151737 A1 | 12/2008 |
| WO | 2009/09829 A1 | 1/2009 |
| WO | 2009039013 A1 | 3/2009 |
| WO | 2009077091 A1 | 6/2009 |
| WO | 2009088608 A2 | 7/2009 |
| WO | 2009/098306 A1 | 8/2009 |
| WO | 2009098291 A1 | 8/2009 |
| WO | 2009098306 A1 | 8/2009 |
| WO | 2009100549 A1 | 8/2009 |
| WO | 2009100550 A1 | 8/2009 |
| WO | 2009101130 A1 | 8/2009 |
| WO | 2009101145 A1 | 8/2009 |
| WO | 2009103759 A1 | 8/2009 |
| WO | 2009106517 A1 | 9/2009 |
| WO | 2009158659 A2 | 12/2009 |
| WO | 2010022069 A2 | 2/2010 |
| WO | 2010077278 A1 | 7/2010 |
| WO | 2010085904 A1 | 8/2010 |
| WO | 2011004333 A1 | 1/2011 |
| WO | 2011/048422 A2 | 4/2011 |
| WO | 2011056375 A2 | 5/2011 |
| WO | 2011075105 A1 | 6/2011 |
| WO | 2011101351 A1 | 8/2011 |
| WO | 2012068321 A1 | 5/2012 |
| WO | 2012072533 A1 | 6/2012 |
| WO | 2012072541 A1 | 6/2012 |
| WO | 2012072554 A1 | 6/2012 |
| WO | 2012072556 A1 | 6/2012 |
| WO | 2012072559 A1 | 6/2012 |
| WO | 2012103316 A1 | 8/2012 |
| WO | 2012103428 A3 | 8/2012 |
| WO | 2012110474 A1 | 8/2012 |
| WO | 2012116948 A1 | 9/2012 |
| WO | 2012126636 A1 | 9/2012 |
| WO | 2012135537 A2 | 10/2012 |
| WO | 2012/160104 A2 | 11/2012 |
| WO | 2012146674 A1 | 11/2012 |

(56) References Cited

FOREIGN PATENT DOCUMENTS

| | | |
|---|---|---|
| WO | 2012152668 A1 | 11/2012 |
| WO | 2012152694 A1 | 11/2012 |
| WO | 2012152703 A1 | 11/2012 |
| WO | 2012152704 A1 | 11/2012 |
| WO | 2012160156 A2 | 11/2012 |
| WO | 2012160167 A1 | 11/2012 |
| WO | 2013/016376 A2 | 1/2013 |
| WO | 2013019850 A2 | 2/2013 |
| WO | 2013033227 A2 | 3/2013 |
| WO | 2013092934 A1 | 6/2013 |
| WO | 2013167494 A1 | 11/2013 |
| WO | 2014005953 A1 | 1/2014 |
| WO | 2014090745 A1 | 6/2014 |
| WO | 2014179774 A1 | 11/2014 |
| WO | 2014191038 A1 | 12/2014 |
| WO | 2014204457 A1 | 12/2014 |
| WO | 2014204894 A2 | 12/2014 |
| WO | 2015018787 A1 | 2/2015 |
| WO | 2015022295 A2 | 2/2015 |
| WO | 2015032745 A1 | 3/2015 |
| WO | 2015074641 A1 | 5/2015 |
| WO | 2015118358 A1 | 8/2015 |
| WO | 2015164645 A1 | 10/2015 |
| WO | 2015164650 A1 | 10/2015 |
| WO | 2016/034683 A1 | 3/2016 |
| WO | 2016034683 A1 | 3/2016 |
| WO | 2016055445 A1 | 4/2016 |
| WO | 2016067179 A1 | 5/2016 |
| WO | 2016071483 A1 | 5/2016 |
| WO | 2016154413 A1 | 9/2016 |
| WO | 2016172182 A1 | 10/2016 |
| WO | 2017080814 A1 | 5/2017 |
| WO | 2017129191 A1 | 8/2017 |
| WO | 2017160625 A1 | 9/2017 |
| WO | 2017160626 A1 | 9/2017 |
| WO | 2017211850 A1 | 12/2017 |
| WO | 2017214392 A1 | 12/2017 |
| WO | 2017214405 A1 | 12/2017 |
| WO | 2017214415 A1 | 12/2017 |
| WO | 2017214424 A1 | 12/2017 |
| WO | 2018002314 A1 | 1/2018 |
| WO | 2018018166 A1 | 2/2018 |
| WO | 2018024625 A1 | 2/2018 |
| WO | 2018029238 A1 | 2/2018 |
| WO | 2018096149 A1 | 5/2018 |

OTHER PUBLICATIONS

Written Opinion Corresponding to PCT/EP2017/080535 dated Jan. 2, 2018.

* cited by examiner

DEVICE FOR DISPENSING A SUBSTANCE

FIELD OF THE INVENTION

The present invention relates to a device for dispensing a substance, in particular to a patient.

BACKGROUND OF THE INVENTION

In the administration of liquid formulations of pharmaceutical active substances, it is in most cases necessary to deliver well-defined quantities of substance. Medicaments often have to be injected into the body of a patient. For parenteral injection, use is commonly made of hypodermic syringes, drug pens or drug pumps.

Particularly in the case of preparations that cannot be stored in a liquid presentation form over a long period of time, there are strict requirements applying to their administration. For example, active substances that are produced in particular by biotechnology can often only be stored in a freeze-dried form over a long period of time. Lyophilisates of this kind are dissolved in an injection solution, for example an aqueous saline solution, just shortly before being administered, and they are then drawn up into a syringe, for example. However, such a procedure may also be necessary in the case of preparations that require two liquids to be mixed.

A number of devices for preparing injection solutions of this kind are already known in the prior art. For example, WO 2016/034683 A1 describes a pen with which a patient can carry out the reconstitution and administration of a lyophilisate himself. Said pen is designed for use with what is called a dual-chamber carpule. The latter is substantially identical to a standard carpule but has two stoppers mounted displaceably in the carpule body, as a result of which two compartments arranged one behind the other are formed in the carpule body. The lyophilized pharmaceutical active substance and the injection solution are made available in these compartments. By actuation of the pen, the two compartments can be fluidically connected to each other, as a result of which the injection solution flows across into the compartment with the lyophilisate, and the latter, is thereby dissolved. By further actuation of the pen, the reconstituted active substance can be injected via an injection cannula. A pen of this kind facilitates the handling of the active substance compared to a conventional hypodermic syringe.

However, a disadvantage of such a system is that the sequential arrangement of the two compartments along the longitudinal axis of the dual-chamber carpule makes the pen somewhat unwieldy. This is a problem particularly in indications that require a patient to carry a medicament around with him over quite a long period of time, since he will need this medicament in the event of a medical emergency that may be expected in view of his condition. Such an emergency may be, for example, an anaphylactic shock, a stroke, an epileptic fit or a myocardial infarct. A further disadvantage of the above-described pen is that the actual injection has to be carried out by the patient or by another person who is present and who can help. When a medical emergency occurs, it is much more difficult for a patient to perform an exercise in which he himself has been trained at best to an amateur level, in addition, the above-described described pen does not permit reconstitution, or controlled reconstitution, independently of its orientation relative to gravity.

The prior art also includes WO 86/06967. The latter document deals with an automatic injection device for reconstitution of a lyophilisate prior to subcutaneous administration. In said document, a nose portion of the device is applied to the skin and an activation button is then pressed. Following release of a compressed spring, force is exerted on a piston and housing system, as a result of which the hypodermic needle emerges from the nose portion through a resilient sheath and penetrates the muscle tissue of the patient. However, usability studies have shown that this step causes the patients real effort, and also that a stiff cannula remaining in place may be unpleasant for the patients, particularly over a long injection time or in cases of frequent penetration of the skin for administration of medical products.

SUMMARY OF THE INVENTION

It is therefore the object of the present invention to overcome the disadvantages of the prior art. It is in particular an object of the present invention to make available a device which serves to dispense a substance, in particular to a patient, and which is easier to handle. This relates in particular to the transportation of the device if the latter is to be worn on a person's body. However, the actual manageability of the device when dispensing a substance, in particular to a patient, is also intended to be made easier. Through the use of a system composed of puncture cannula and indwelling cannula/the injection is intended to be free of pain, gentle and safe.

These objects are achieved by a device having the features of the independent claim(s). The device for dispensing a substance, in particular to a patient, comprises a cylindrical first container containing the substance, and a second container containing a liquid. In addition, the device comprises an injection device and transfer means for transferring the liquid from the second container to the first container and from the first container to the injection device. The first container has, at a first end, an attachment element and a piston that is displaceable between the first end and a second end. By displacement of the piston toward the first end of the first container, a liquid contained therein can be dispensed via the injection device.

The injection device may be suitable for dispensing by a subcutaneous, intramuscular, intravenous, intra-arterial, intra-articular, intracardiac intracutaneous, intra-osseous, intraperitoneal, intrapulmonary, intrathecal, intravitreal or intracelomic route. The injection device can be a simple hypodermic cannula or, as set out in detail below, can be in the form of more complex devices.

This embodiment of the device permits many possibilities concerning the nature of the second container and the positioning of the latter relative to the first container. It is thus possible to make available a device that is much more compact and, if necessary, also more ergonomic than those known in the prior art. The manageability of the device is thus enhanced. Moreover, reconstitution of a lyophilisate is possible independently of the orientation of the device relative to gravity.

The injection device moreover comprises a puncture cannula. In addition, the injection device can comprise an indwelling cannula, and, in an starting position, a distal end region of the puncture cannula extends coaxially in the interior of the indwelling cannula. An injection device with indwelling cannula is designed in such a way that the puncture cannula withdraws again directly after the puncture has been made. Only the indwelling cannula remains in the injection site for a long or short period of time. On the one hand, this reduces the unpleasantness felt by a patient. On the other hand, after use of the device, there is no risk of injury from the puncture cannula. An additional needle guard is not needed.

However, if the injection device comprises only a puncture cannula, it is also conceivable that the latter withdraws independently after the injection has taken place. If the device is placed on the body of a patient, it is also conceivable for the puncture cannula to withdraw independently when the device is removed from the body of the patient.

Moreover, the device according to the invention has the advantage that, after the carpule contents have been mixed by an action of the user and the device has been placed on the body, only a second operation by the user is needed in order to trigger the subsequent steps. In particular, the second action can entail pressing a button. By pressing the button, the deployment of the needle, the withdrawal of the puncture cannula and the injection of the mixture can be performed in one and the sane logical sequence. The purely mechanical sequence is controllable by the displacement of a control cam in relation to at least one runner and optionally in relation to further lever elements. In this way, mechanical forces can be transferred to component parts of the device in a predefined time sequence. The present invention thus involves a minimum amount of handling on the part of the user. The operation of the device is thus easier, more comfortable and less prone to error.

The injection device can comprise a first and a second displaceably mounted runner. The first runner can be connected to the puncture cannula and the second runner can be connected to the indwelling cannula. The infection device can moreover comprise a control element which is movable over a predefined control range and which can be operatively connected to the first runner and second runner in order to move them. The control element can be configured in such a way that, in a first part of the control range, it effects a co-directional and in particular simultaneous displacement of the two runners and thus a placement of the indwelling cannula. The control element can moreover, be configured in such a way that, in a second part of the control range, it effects a blocking of the second runner, thereby holding the indwelling cannula in a dwell position, and a rearward displacement of the first runner, hence a withdrawal of the puncture cannula from the distal end region of the indwelling cannula to an end position.

By virtue of this mechanical configuration of the injection device, placement of the indwelling cannula, assisted by the puncture cannula, can be reliably followed by a withdrawal of the puncture cannula. The mechanism requires only a small number of individual parts, as a result of which it can be produced cost-effectively and is reliable in use.

The runners can be mounted displaceably via a guide device, preferably via a common guide device, in particular via a linear guide. The use of a common guide device makes it possible to further reduce the number of the individual parts of the injection device. In particular, a linear guide permits a simplification of the mechanism.

Thus, the runners can be mounted displaceably via a common linear guide, and the linear guide can be oriented in an application direction parallel to the distal end regions of the puncture cannula and of the indwelling cannula. Therefore, the linear guide predetermines not only the direction of displacement of the first and second runners, but also the application direction of the injection device. This direction can thus be defined in advance and adapted to the particular use of the device. For example, it is possible to configure the injection device in such a way that the indwelling cannula is applied substantially perpendicularly under the skin of the patient.

The control element can be mounted so as to be movable, in particular displaceable, in a direction perpendicular to that of the linear guide. This permits an optimal transmission of force from the control element to the first and second runners in both directions.

The control element can be configured as a displaceable cam carrier. A cam carrier has the advantage that almost any movement that is representable via a constantly differentiable function can be predefined by it. In addition, by means of a suitably selected control element, it is possible to represent zero settings and discontinuity settings of a function.

The control element can be configured as a pair of congruent, displaceable cam carriers, said pair acting on both sides on the runners. This allows the force to be transmitted in a particularly effective manner from the control element to the runners. Since the force transmission is realized on both sides, it is possible to prevent a torque from being at the same time transmitted to the runners. A tilting of the runners in a guide device can thereby be avoided.

The control element can comprise a first portion and a second portion. The first portion can effect a co-directional, in particular simultaneous, displacement of the two runners, hence a placement of the indwelling cannula. The second portion can effect a blocking of the second runner, hence a holding of the indwelling cannula in a dwell position, and also a withdrawal of the first runner, hence a withdrawal of the puncture cannula from the distal end region of the indwelling cannula to an end position. In particular, different sides of the second portion can here act on the first runner and on the second runner. Through the division of the control element into two portions, it can be designed particularly simply in terms of its geometry.

The control element can be pretensioned via a spring element. This allows an independent displacement of the control element, to be effected in a structurally simple manner, without a further, separate drive being necessary for this purpose. Alternatively, the control element could also be driven by expanding gas.

The control element can have an additional cam surface, in particular in a second part of the control range directed away from the drive. When moved further on, this cam surface can come into operative engagement with a lever element located in the direction of movement. The lever element is thus movable from a first position to a second position, as a result of which a further function of a corresponding device can be triggered, for example, a valve device or delivery device can be activated in order to convey a fluid to the injection device.

The substance in the first container can be a solid, in particular a lyophiphilisate, or a liquid, in particular a solution. The described device thus alternately permits the dissolving of a solid, in particular the reconstitution of a lyophilisate, or also the mixing of two liquids. The device is thus versatile in its use.

The first container can be a standard carpule, a vial or a conventional hypodermic syringe. Such containers are established in the prior art and meet the regulatory requirements, particularly in the case of pharmaceuticals which are usually subject to approval and registration procedures.

The second container can likewise be cylindrical, with an attachment element at a first end and with a piston displaceable between the first end and the second end. Containers of this kind are also in widespread use for liquids, for example in the form of carpules with an injection solution, and are commercially available from a large number of suppliers. Thus, when using a device of this kind, it is possible to have recourse to standard components.

However, it is also conceivable for the second container to be collapsible, for example in the form of a tube, a bag or a bellows. This permits further embodiments of the device according to the invention that are particularly advantageous in terms of a compact structure.

With a cylindrical design, the second container can be arranged parallel to the first container, in particular co-directional thereto. It is thus possible, for example, for two carpules to be used with the device. On account of their arrangement relative to each other, the device as a whole is much less bulky than those known in the prior art.

However, it goes without saying that the present invention is not limited to two containers. For example, in addition to having a first container with a lyophilisate and a second container with a solvent, a device according to the invention can also comprise a third container with a diluent. The solvent and the diluent are in most cases aqueous solutions. The variants discussed above tor the second container apply as regards the configuration of the third container and each further container. In such a configuration, it is possible to transfer the diluent, like the solvent, from the third container to the first container and then onward to the injection device. However, it may also be advantageous if the device is not designed to transfer the liquid from the first container to the injection device, and instead the liquid is transferred from the first container to the third container and from there onward to the injection device.

The piston of the first container and if appropriate also the piston of the second container can be displaceable by displacement means, it is thus possible to achieve an independent transfer of the liquid from the second container to the first container or also from the first container to the injection device.

The piston of the first container and if appropriate also the piston of the second container can be pretensioned by a respective spring element and thus be displaceable. Spring elements represent a cost-effective and reliable design of displacement means. This is of particular importance if the device is provided to be used just once.

The piston of the first container and if appropriate also the piston of the second container can be held back counter to the pretensioning via retention means, it goes without saying that this can be realized directly or indirectly. That is to say, the retention means do not necessarily nave to act on a piston, and instead they can also act on a spring element or another component of the device. Through the use of retention means, it is possible to ensure that a displacement of the pistons by the pretensioning occurs only when this is desired. However, in the case of an indirect action of the retention means, the one or more spring elements can also be pretensioned before the first container and if appropriate also the second container is/are inserted into the device.

However, the piston of the first container and if appropriate also the piston of the second container can be displaceable via a linear drive, in particular a spindle drive or a cam mechanism. In this way, an electronic control of the piston movement can be realized. This is particularly advantageous since it permits an extremely precise dosing of the substance in the course of dispensing the latter, if necessary also over a long period of time.

However, it is also possible to use a pneumatic or a hydraulic drive. A pneumatic drive permits many different possibilities in terms of the provision of a pneumatic medium. For example, the latter can be made available in a pneumatic pressure container. However, it is also conceivable for a gas pressure to be built up by a corresponding chemical reaction (gas expansion).

The attachment element of the first container and if appropriate also that of the second container can be configured as a septum. A septum permits a particularly reliable and tight closure of a container. However, the container can simply be attached.

The septum of the first container and if appropriate also the septum of the second container are able to be penetrated by penetration means, in particular by displacement or by torsion of the first container and if appropriate also of the second container relative to the one or more penetration means. Embodiments are also possible in which the penetration means is displaceble relative to the container and the penetration is effected by this movement. By penetration of a septum, attachment of the first container and if appropriate also of the second container to the device can be achieved in a particularly reliable and cost-effective way.

The one or more penetration means can be configured as hollow cannulas, in particular with an oblique ground edge. Direct transfer of a liquid from a container into a hollow cannula can thus be achieved. Further fluid-conveying parts for attachment to the container are omitted.

In order to reduce the risk of contamination of the substance to be dispensed, it is advantageous, especially in sterile applications, if the penetration means are each provided with a flexible protective cap or protective sleeve, which is likewise penetrated together with a septum. The use of a protective cap or protective sleeve of this kind permits in particular a final assembly of the device under non-sterile conditions.

The septum of the first container, if appropriate also that of the second container, can be penetrated by displacement, in particular with the displacement means for the one or more pistons of the first and/or second container. In this embodiment, a movement of fluid-conveying parts inside the device is avoided. In addition, the displacement means can at the same time be used to displace the one or more pistons and to attach the one or more containers to the device.

The first container can be brought into fluidic communication with the second contains and the injection device via the attachment element. Since any transfer of fluid from or to the first container is realized via the attachment element, further fluid connections are not provided.

The first container can be brought into fluidic communication alternately with the second container or the injection device via a valve arrangement. In this way, the flows of fluid from or to the first container can be controlled in a targeted manner.

The injection device and if appropriate also the displacement means can be activatable via activating means, wherein the activating means are designed in particular to release the retention means. Through the use of activating means, the actuation of the device can be made easier, in particular for a patient.

The injection device and the displacement means for displacing the first piston can be activatable via the same activating means. In this way, the whole injection process can be activated by actuation of a single activating means.

It goes without saying that the control element can also be held back counter to the pretensioning by retention means. As has already been explained, these retention means can be released via activating means, in particular via the sane activating means as for the above-described retention means.

However, the control element can also be movable via a screw mechanism, in particular via a spindle drive. In this way, the control element can easily be moved by a rotary drive with the necessary gear reduction.

The control element can also have further came surfaces for triggering further mechanisms. For example, the control element can act on a lever element in a second part of the control range, as a result of which the lever element is displaced or rotated. As a result, a further function of a corresponding device can be controlled. For example, the activation of a valve device or conveying device for conveying a fluid to the injection device.

The device can also have further cam surfaces that are not mounted directly on the control element. For example, a cam surface can be formed integrally with the stop element, which is connected to the control element via a rod. Upon displacement of the control element, such a cam surface is able to follow the control element and engages in a slide in the course of its movement. In this way, a further retention means for example can be released, and a displacement means previously held in a tensioned position is able to relax.

In one embodiment, the second runner can be configured as a holding plate. A holding plate has the advantage that it is easier to manufacture than an injection molded part. Moreover, with the same wall thickness, it has a greater mechanical load-bearing capacity. Furthermore, if so desired, it can have a certain spring action.

A transition from the puncture cannula to the indwelling cannula can be sealed off with a sealing element which is squeezed in the dwell position, in particular by a wall portion of a dosing device and the second runner. A particularly fluid-tight transition from the puncture cannula to the indwelling cannula can be achieved in this way. It goes without saying that this design of the infection device can also be realized independently of other features of the device.

The puncture cannula can be formed in one piece as a continuous hollow needle, in particular made of steel. This design allows the puncture cannula to assume simultaneously a conveying function and a penetrating function. In particular, sealing problems between different line sections can thus be avoided. The proximal end region of the puncture cannula can be fixed in position and rigid. A reliable fluid connection, for example to the valve device, can thus be ensured.

The device can comprise a housing with an external contact surface via which the device can be applied in particular to the body of a patient. In a preferred embodiment, the device can be affixed to the body via a self-adhesive plaster. The self-adhesive plaster can already be applied to the external contact surface of the device and can be exposed by detachment of a protective film. With such a configuration of the device, it is possible to ensure chat an injection can be carried out in a particularly reliable and user-friendly manner. Moreover, this allows a substance to be dispensed according to a predefined schedule and/or over a lengthy period of time, in particular in the case of mobile patients. Depending on the indication, however, it is also conceivable for a substance to be dispensed to a patient even when, for example on account of an acute medical emergency, he is no longer able to self-inject.

The puncture cannula and if appropriate also the indwelling cannula can be arranged substantially inside the housing in the starting position and can be deployed from the housing through an application opening in the contact surface. In this way, an injection can take place fully automatically, particularly in the case of a device placed on the body of a patient. This facilitates the handling of the device by a patient.

A further aspect of the invention concerns the use of an above-described device for dispensing a substance, in particular to a patient.

A method for filling a container with a lyophilisate is also described below. The container is cylindrical and comprises a piston displaceable between a first end and a second end. Said container can in particular be a carpule. At the start of the method, the piston is positioned between the first end and the second end in such a way that a volume for receiving a liquid is obtained between the piston and the first end. The volume is at least partially filled with a solution, in particular an aqueous solution, containing a substance. The container is then cooled, in such a way that the solution goes from the liquid to the solid state of aggregation. Applying a vacuum to both sides of the piston results in sublimation of the solvent, which escapes from the container at the first end. The non-volatile fractions of the solution remain as lyophilisate in the container. At the end of the sublimation process, the first end of the container is closed with an attachment element, in particular with a septum.

In a first variant of the method, the container is returned to atmospheric pressure after closure, wherein the piston is freely displaceable in the container. As a result of the pressure difference on both sides of the piston, the latter is displaced toward the first end of the container.

In a second variant of the net method, the container is returned to atmospheric pressure after closure, wherein the piston is not freely displaceable in the container, being held for example via a piston rod. In this way, a vacuum or underpressure remains in the piston.

The reheating of the container can take place before or after the change to atmospheric pressure.

The method described has the advantage that a container, in particular a carpule, filled with a lyophilisate can be made available in a reliable and efficient way, said container being substantially free of gas, in particular free of air. Such a container is advantageous in particular in combination with an above-described device for gas-free or air-free reconstitution of the lyophilisate.

The control element of the device according to the invention can additionally be configured as a displaceable cam carrier. The control element can in particular comprise a linearly displaceable carriage on which at least one cam carrier is formed. Particularly preferably, the displacement direction of the carriage runs parallel to the longitudinal axes of the first and the second container.

The use of a displaceable cam carrier, and in particular of a linearly displaceable carriage with one or more cam carriers, has the advantage of ensuring that the steps are performed in the correct chronological sequence in a simple and error-resistant manner.

The sequence, which is controlled by the displaceable carriage, will become clearer from the drawings described below. In summary, the sequence of the control element can comprise the following steps: Firstly, two runners, of which one is operatively connected to the puncture cannula and the other to the indwelling cannula, are pushed jointly in the direction of the patient's tissue. Secondly, the runner operatively connected to the indwelling cannula is locked in position, while the runner operatively connected to the puncture cannula is deflected away again from the patient's tissue and further into the interior of the housing. Thirdly, an additional cam surface of the cam carrier can be operatively connected to a lever element, as a result of which the lever element is displaced and/or a rotation takes place about the axis of rotation of the lever element. The lever element can thus control further functions of a corresponding device, for example an activation of a valve device or conveying device. Fourthly, the injection can be triggered at the same time as or shortly after the actuation of the lever element, for example by the release of a spring, which was previously secured in a tensioned position by a displaceable retention element. The sequence is clocked and automated by the operating sequence of the control element. Two concrete illustrative embodiments will become clear from the drawings described below. The direction of displacement along the longitudinal center axes can be chosen in order to make available a device that saves space and is therefore handy for the user and easy to transport.

BRIEF DESCRIPTION OF THE DRAWINGS

Further advantages and individual features of the invention will become clear from the following description of two illustrative embodiments and from the schematic drawings, in which.

DETAILED DESCRIPTION OF THE PREFERRED EMBODIMENTS

Figure 1:
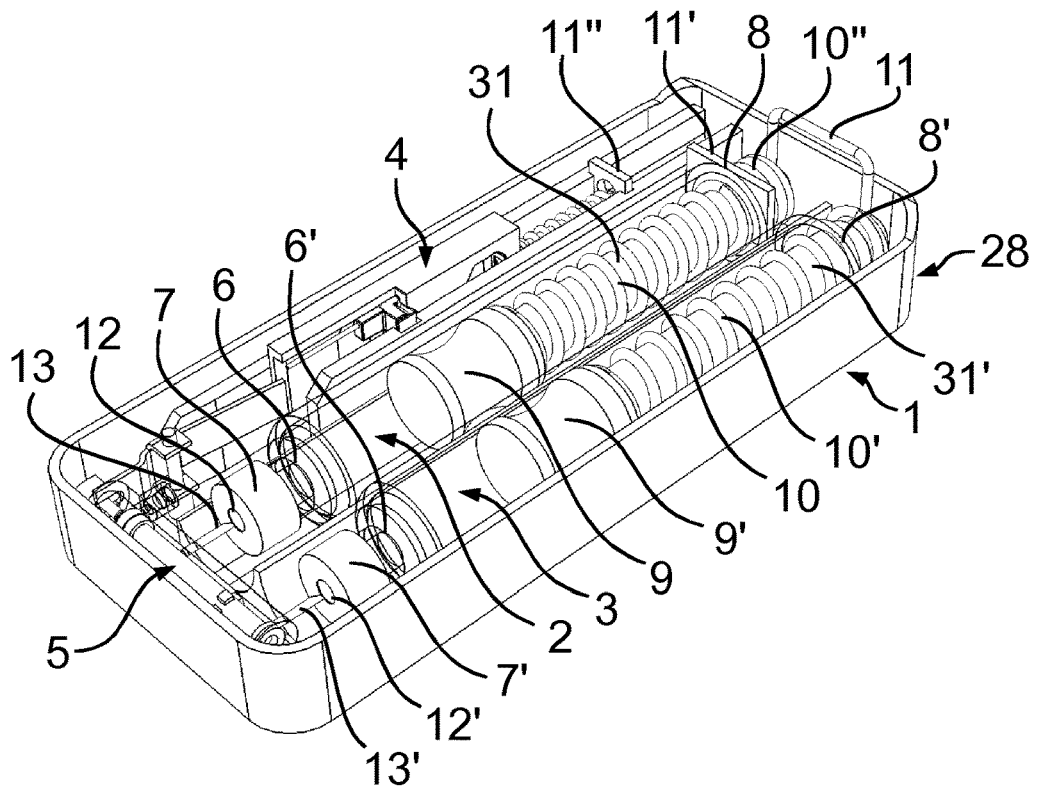
FIGS. 1 to 6 show perspective views of a first illustrative embodiment of a device according to the invention in various operating states.

As will be seen from FIG. 1, a first illustrative embodiment of a device 1 according to the invention has a first container 2 and a second container 3, each in the form of a carpule. To make matters clearer, the carpule bodies of the containers 2, 3 are shown as transparent. In addition, the device 1 comprises an injection device 4 and transfer means 5. To make matters clearer, the outer housing of the transfer means 5 is also shown as transparent. The two containers 2 and 3 each have a first end 6, 6' and a second end 8, 8'. Inside the containers 2 and 3, a respective piston 9, 9' is mounted displaceably between the ends 6, 6' and 8, 8'. The containers 2 and 3 are each closed off at the ends 6 and 6' by an attachment element 7, 7'. The pistons 9, 9' are pretensioned indirectly via the piston rods 31, 31' and are displaceable by the spring elements 10, 10'. The pistons 9, 9' are held back by the retention elements 11, 11', which each engage on the piston rods 31, 31'. Two spring elements 10 and 10" engage on the first container 2. Whereas the spring element 10 serves to displace the piston 9, the spring element 10" only has the function of displacing the first container 2. The spring elements 10 and 10' are held back selectively via the retention means 11 and 11'. The attachment elements 7, 7' of the first container 2 and second container 3 each have a septum 12, 12'. The septums 12, 12' are able to be penetrated by the penetration means 13, 13'. The device 1 is accommodated in a housing 28.

Figure 2:
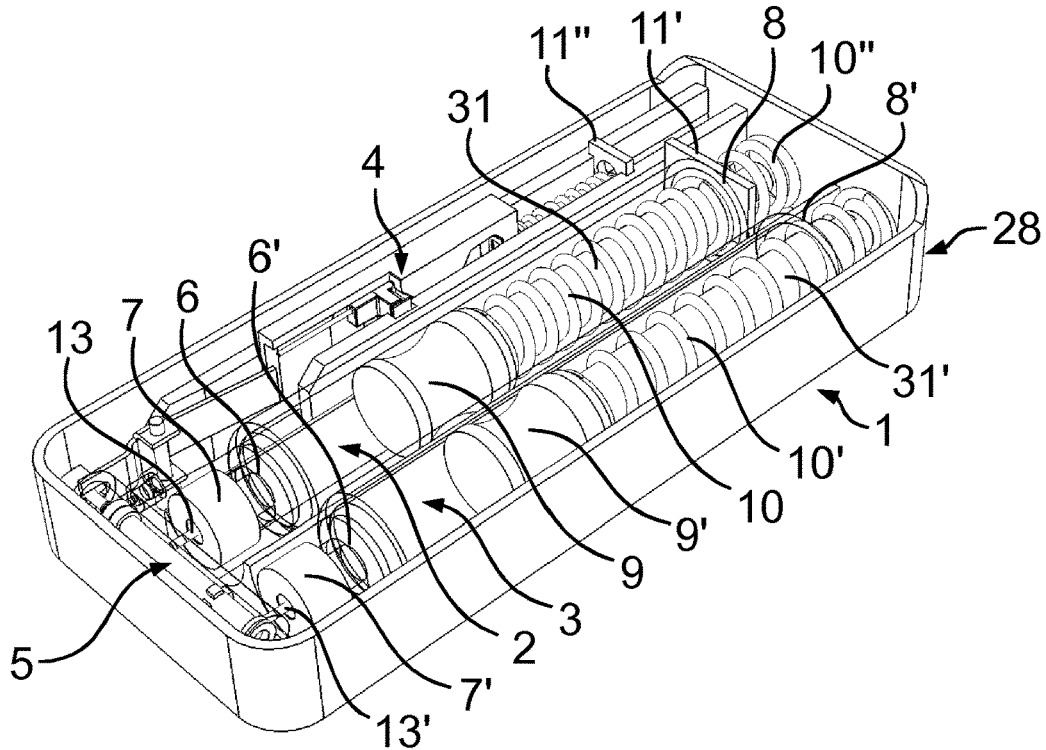

FIG. 2 shows the device 1 from FIG. 1 after the retention means 11 has been removed. It will be seen that the spring elements 10', 10' have caused a displacement of the containers 2, 3 and have therefore caused the penetration elements 13, 13' to penetrate the septums 12, 12'. The pistons 9, 9' inside the containers 2, 3 have still not been displaced at this time.

Figure 3:
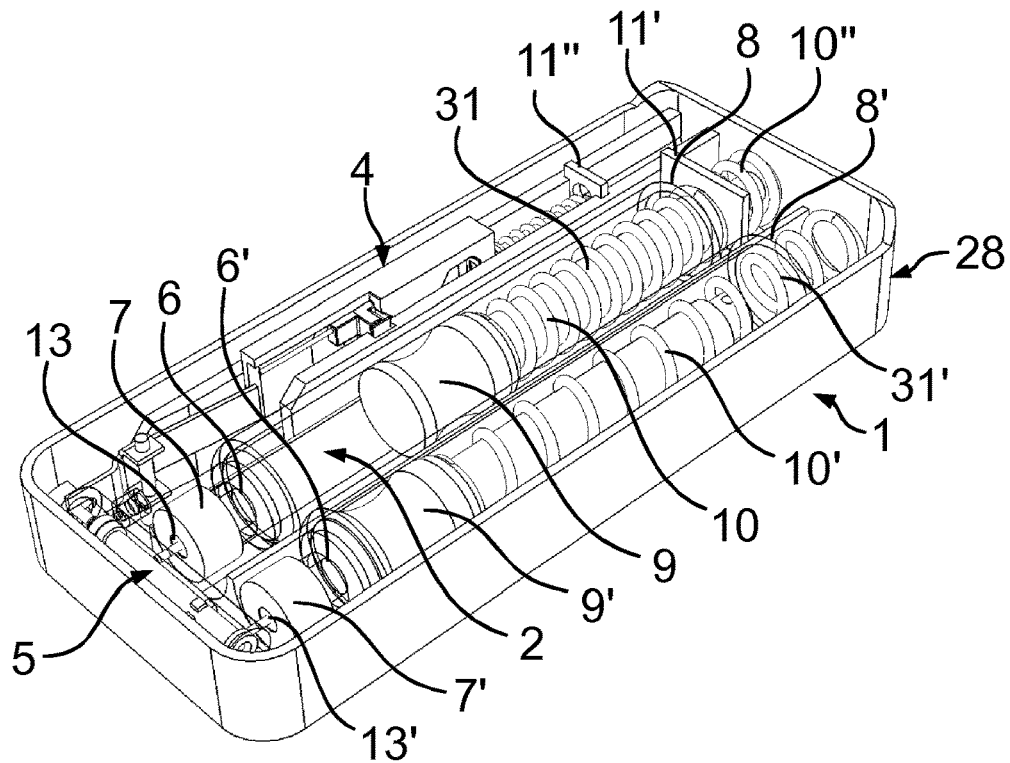

FIG. 3 shows the device 1 from FIGS. 1 and 2 after the piston 9' of the second container 3 has been displaced by the spring element 10' all the way to the first end 6' of the second container 3. The liquid (not shown) previously present in the container 3 has been transferred into the first container 2 via the transfer means 5. The first container 2 was previously under vacuum and contained a lyophilisate (not shown). Accordingly, the first container 2 was able to receive the entire content of the second container 3 without requiring a displacement of the piston 9. In this way, the lyophilisate comes to be dissolved in the liquid. In order to prevent an inadvertent displacement of the piston 9 of the first container when the latter is under vacuum, the piston 9 is connected fixedly to the piston rod 31.

Figure 4:
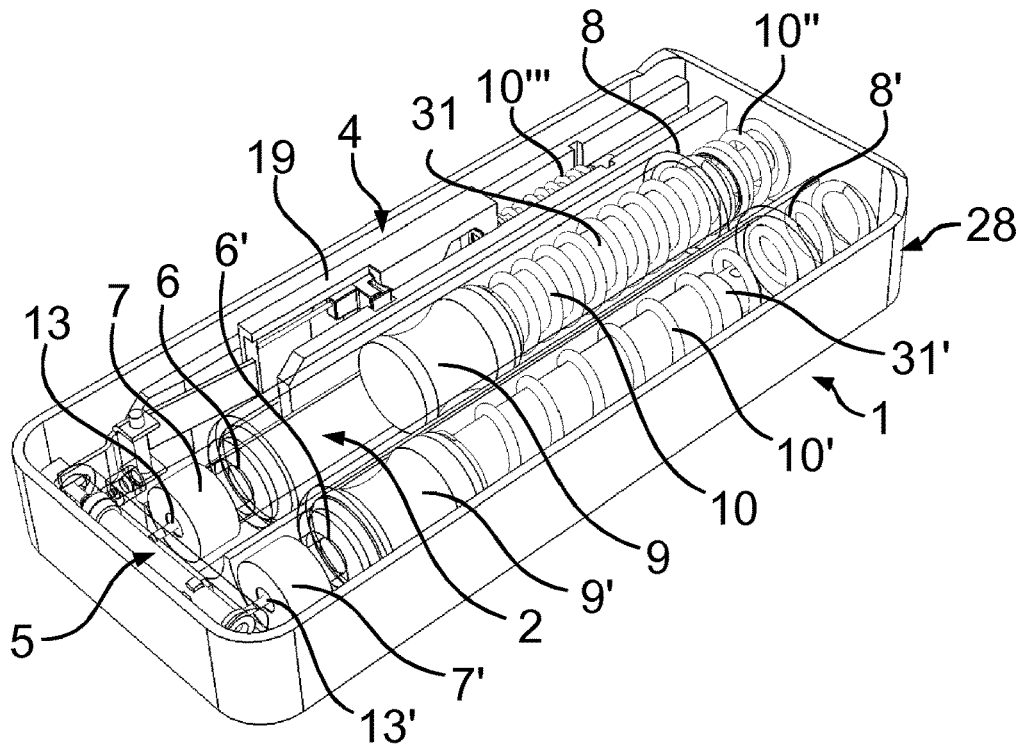

In FIG. 4, the retention means 11', 11" have additionally been removed. The retention means 11' has previously held back the piston 9 of the first container 2, which was pretensioned via the spring element 10. The retention means 11" has previously held back the spring element 10''', via which the injection device 4 was pretensioned.

Figure 5:
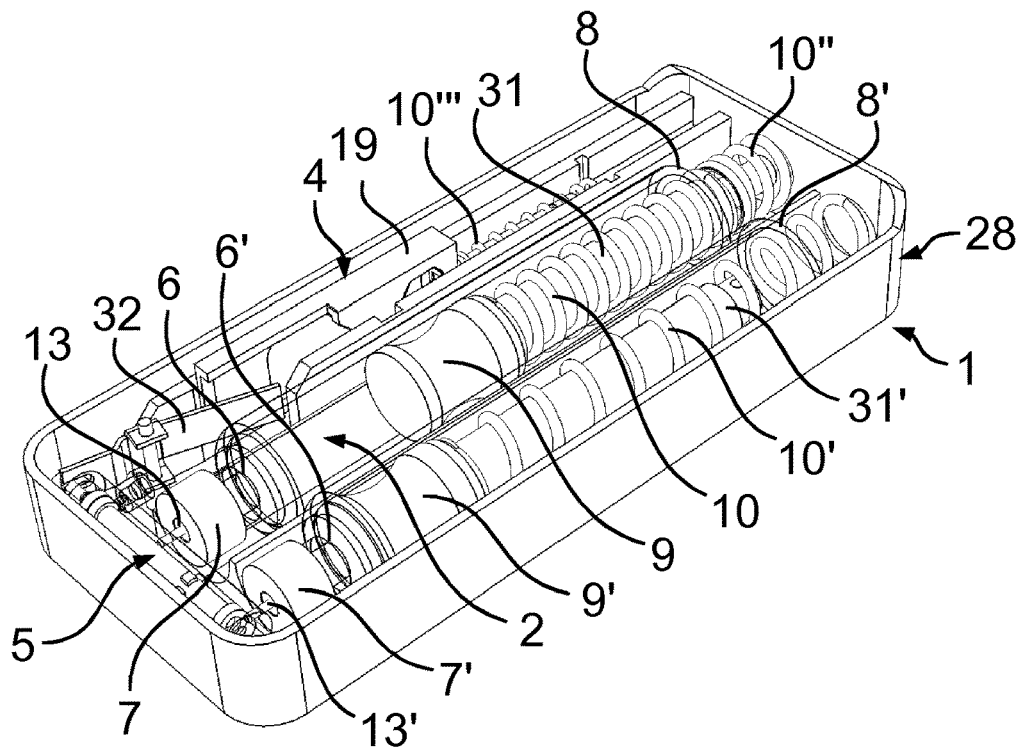

FIG. 5 shows the device 1 after partial displacement of the control element 19 of the injection device 4 by the spring element 10'''. The control element 19 thus acts on the lever 32, as a result of which the valve device of the transfer means 5 is switched. Whereas the first container 2 is in fluidic communication with the second container 3 in a first phase, the first container 2 is later in fluidic communication with the injection device 4. Since the fluid path from the first container 2 to the injection device is freed, the pressure in the first container 2 drops, as a result of which the piston 9 of the first container 2 is now also able to start moving.

Figure 6:
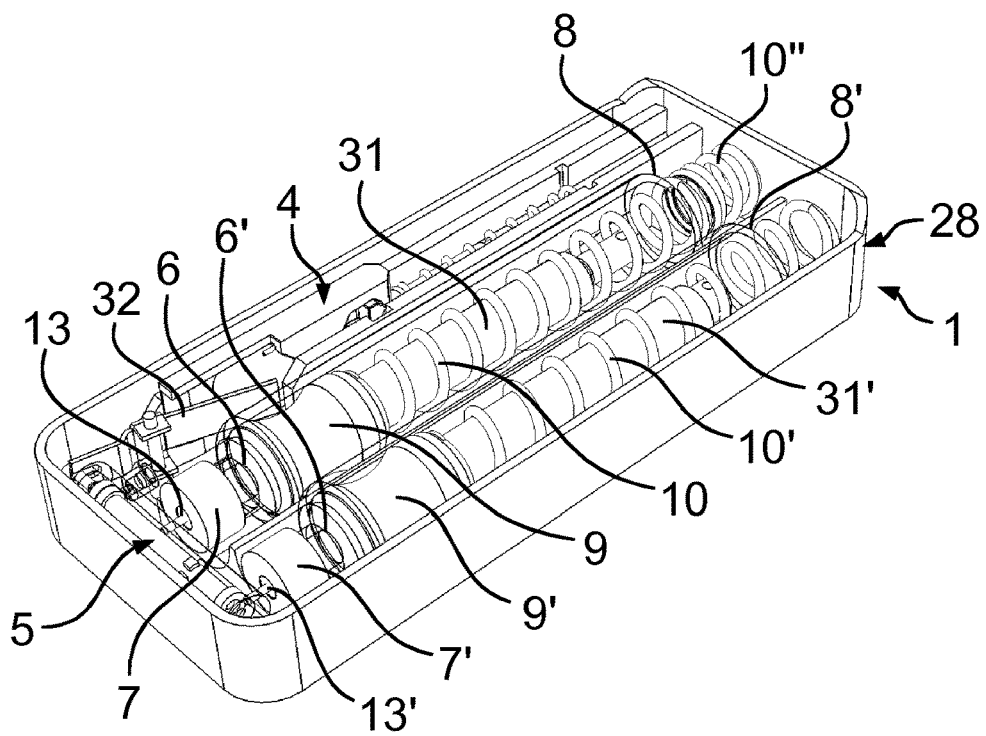

In FIG. 6, the displacement of the piston 9 of the first container 2 to its end position has been completed. In this way, all of the liquid present in the first container 2 has been dispensed via the injection device 4.

Figure 7:
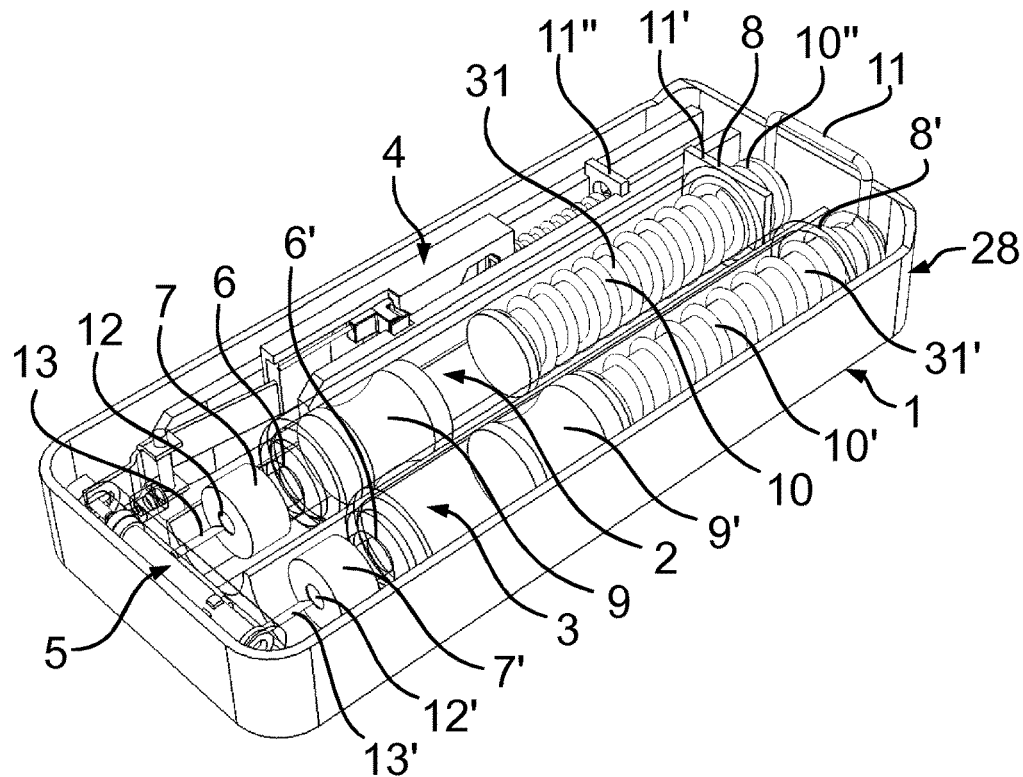
FIGS. 7 and 8 show perspective views of a variant of the illustrative embodiment from FIGS. 1 to 6 in different operating states.
Figure 8:
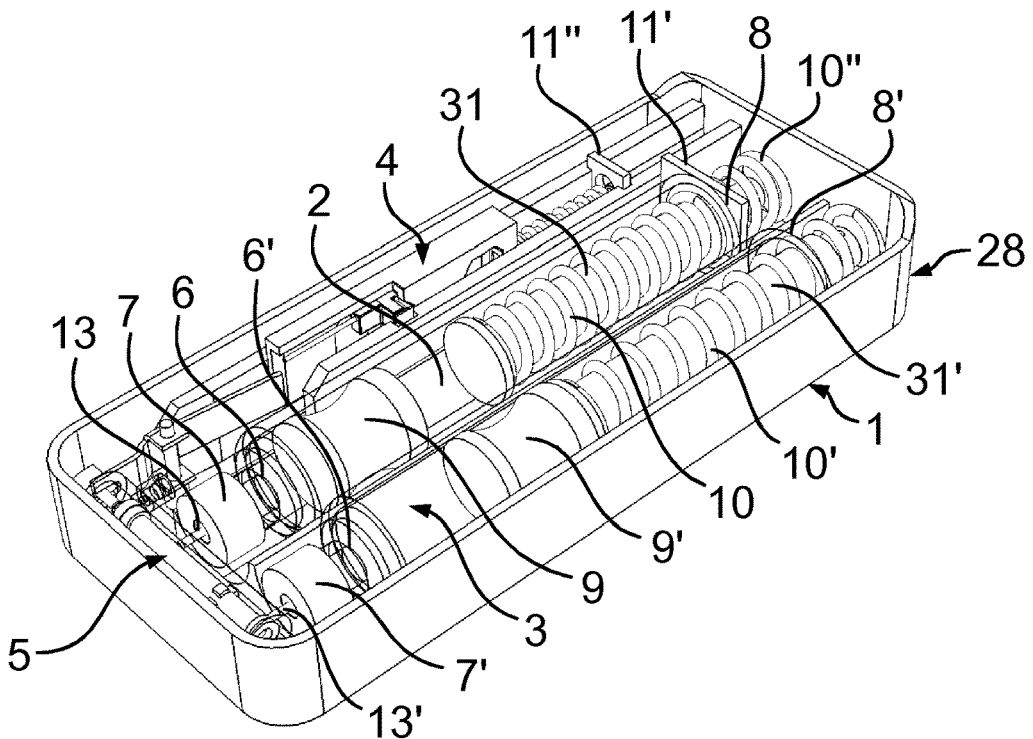

FIGS. 7 and 8 show a variant of the first illustrative embodiment of the present invention from FIGS. 1 to 6. FIGS. 7 and 8 correspond to FIGS. 1 and 2. The two variants of the illustrative embodiment are identical as regards the further course of operation of the device according to FIGS. 3 to 6.

As was explained in relation to the variant discussed above, the first container 2, in which the lyophilisate (not shown) is made available, is initially under vacuum. This is especially important if the aim is to achieve a reconstitution that is as far as possible free of gas, in particular free of air. An alternative solution to this problem is shown in FIG. 7, wherein the piston 9 here almost bears at the first end 6 of the first container 2 and thus minimizes the gas volume remaining in the first container 2. The regaining volume in the first container 2 is chosen such that it is still just able to receive the lyophilisate (not shown). In contrast to the previously discussed variant, the piston 9 of the first container is not connected to the piston rod 31 and is instead freely displaceable in the first container 2.

FIG. 8, analogously to FIG. 2, shows the device 1 after the retention means 11 has been removed. This likewise has the result that the liquid contained in the second container 3 is transferred into the first container 2 via the transfer means 5. The end state of this transfer is shown in FIG. 3. It will be seen that the piston 9 of the first container has been displaced toward the piston rod 31 and now bears on the latter.

An advantage of this variant is that the first container 2 does not have to be made available under vacuum or an underpressure. Therefore, the risk of its content being contaminated by aspiration of ambient air is considerably reduced.

Figure 9:
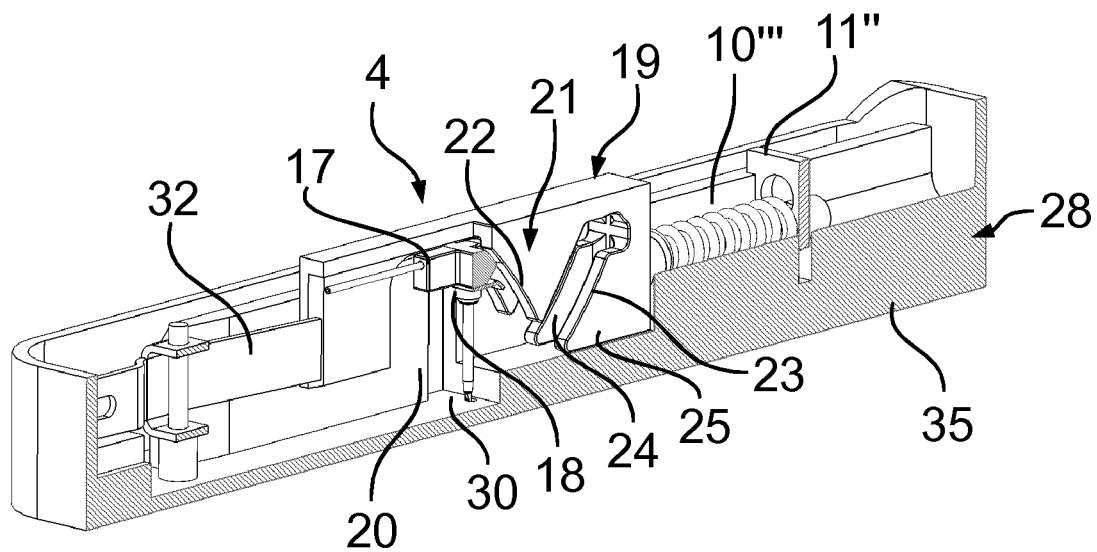
FIGS. 9 to 11 show perspective sectional views of a preferred embodiment of the device from FIGS. 1 to 8, in order to illustrate the operating principle of the injection device.
Figure 10:
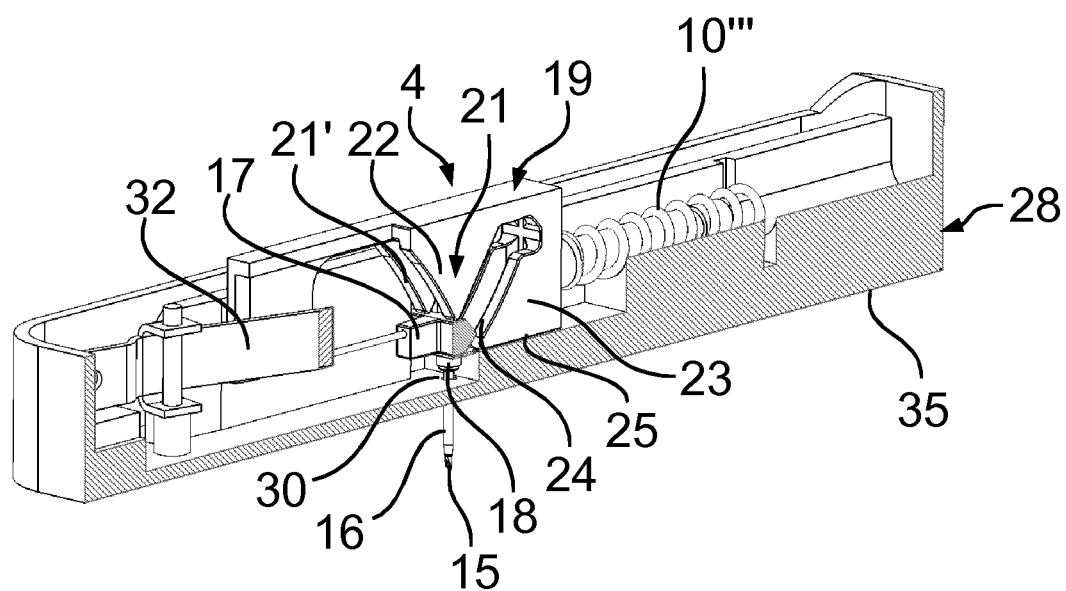

The injection device 1 can be better seen in FIG. 9. It comprises the control element 19, which can be brought into operative connection with a first runner 17 and a second runner 18. The control element 19 is pretensioned via the spring element 10'''. However, it is held back counter to the pretensioning by a retention means 11". Moreover, a linear guide 20 can be seen with which the first runner 17 and the second runner 18 are guided. The control element 19 is formed as a pair of congruent, displaceable cam carriers 21, 21' (FIG. 10). Both portions 22 and 23 of the front carp carrier 21 can be seen. It will be noted that a puncture cannula 15, in the starting position of the injection device 4, runs inside an indwelling cannula 16 (FIG. 10). On the underside of the housing 28, an application opening 30 is provided which extends through a contact face 29 of the housing 28. The second runner 18 is configured as a holding plate, to which is attached a seal which seals off the transition between the application cannula 15 and the indwelling cannula 16.

FIG. 10 shows the first runner 17 and the second runner 18 having reached their lower abutment point. The puncture cannula 15 is thus applied. It can be seen clearly here that the control element 19 is composed of two cam carriers 21, 21'. The control element 19 here has covered approximately half of its intended travel. It can be further displaced by the spring pretensioning. From here on, a first side 24 of the second portion 23 of the cam carriers 21, 21' acts on the first runner 17 and a corresponding side 25 acts on the second runner 18.

Figure 11:
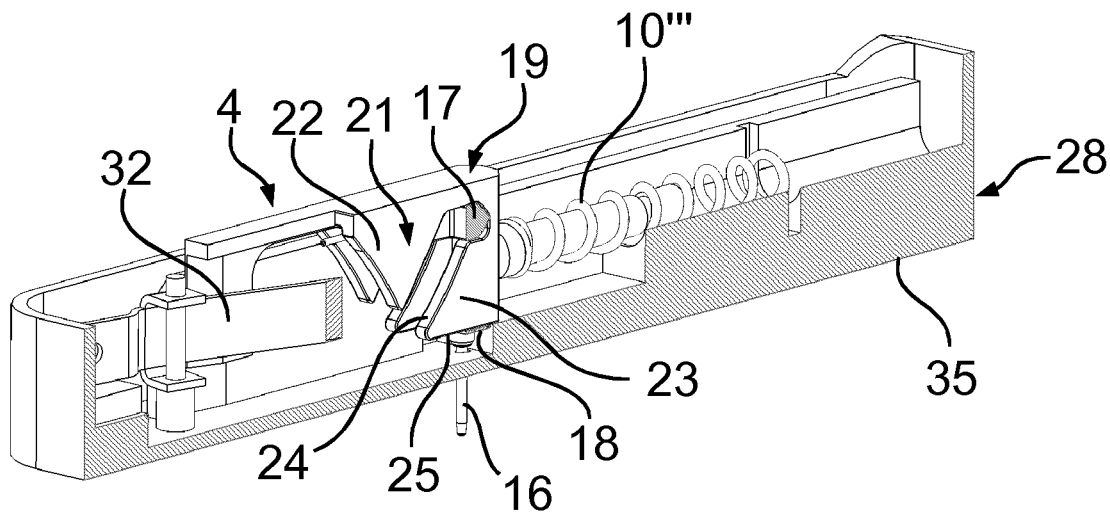

In FIG. 11, the control element 19 has reached its limit stop. It is no longer further movable by the spring element 10'''. The first runner 17 has thus reached its end position. The second runner 18 and also the indwelling cannula 16 are locked in the dwell position. Through the action of the control element 19, the lever 32 has also reached its end position, as a result of which the valve device of the transfer means 5 has been switched.

Figure 12:
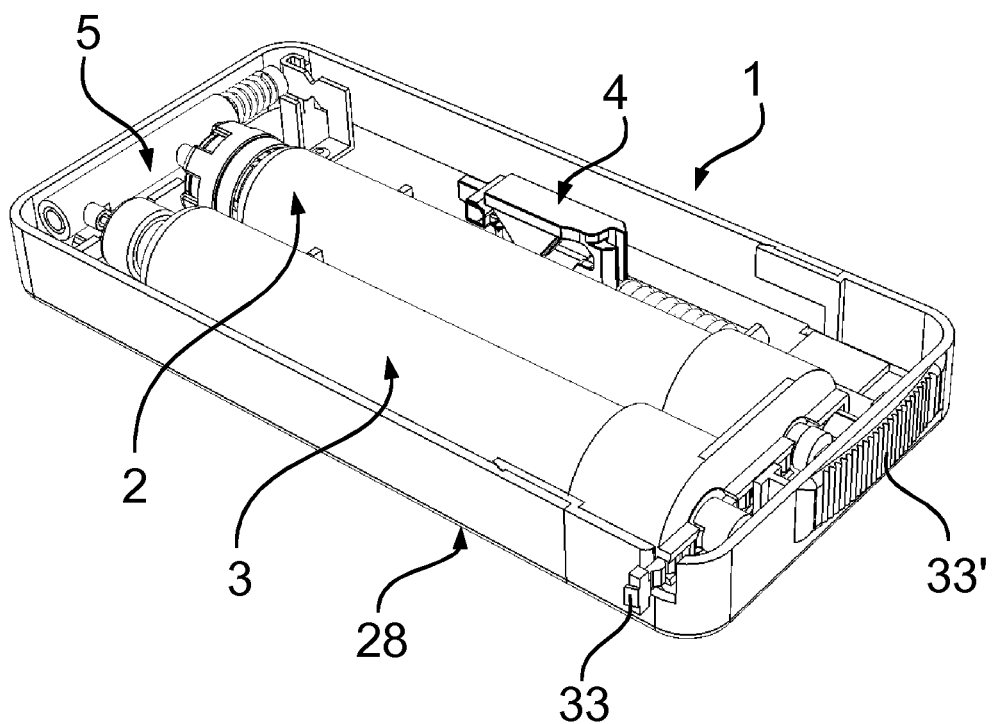
FIG. 12 shows a perspective view of an alternative illustrative embodiment of a device according to the invention.

FIG. 12 shows an alternative illustrative embodiment of a device 1 according to the invention. In this embodiment, the housing 26 provides space, in the region of the injection device 4, for electronic components (although the letter are not shown here). In this embodiment, the device 1 can be activated by the activating means 33, 33', which are configured as easily operated levers or slides.

FIGS. 13 to 16 show a further alternative illustrative embodiment of an injection device 4 according to the invention.

Figure 13:
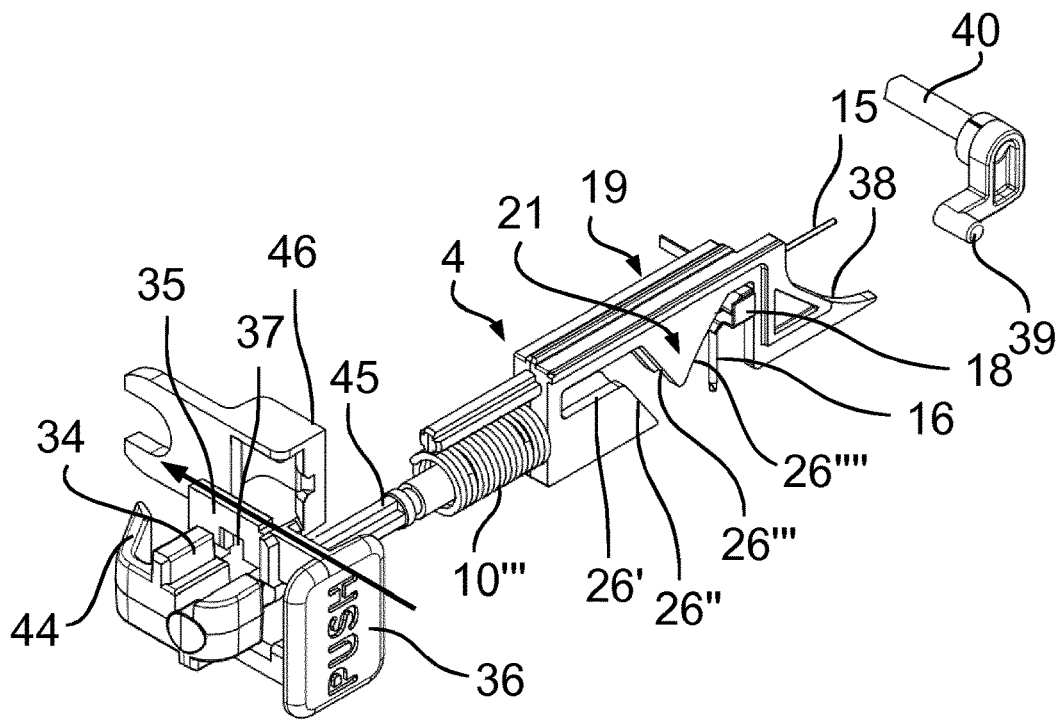
FIGS. 13 to 17 show perspective views of an alternative illustrative embodiment of a device according to the invention in various operating states.

FIG. 13 shows said device 4 in its starting position. The control element 19 is pretensioned via a spring element 10''', which is here configured as a helical spring. The control element 19 is held back counter to the pretensioning by a stop element 34, which bears on a stop plate 35. By actuation of the release button 36 (in the direction of the arrow), the stop plate 35 is displaced in a direction perpendicular to the direction of displacement of the control element 19. In this way, the stop element 34 can slide through the aperture 37 in the stop plate 35 and trigger the actual application procedure.

FIG. 13 additionally shows the cam surfaces 21', 26", 26''', 26'''' of the cam carrier 21, which surfaces predefine the movement of the first runner 17 and of the second runner 16 over the control range.

Figure 14:
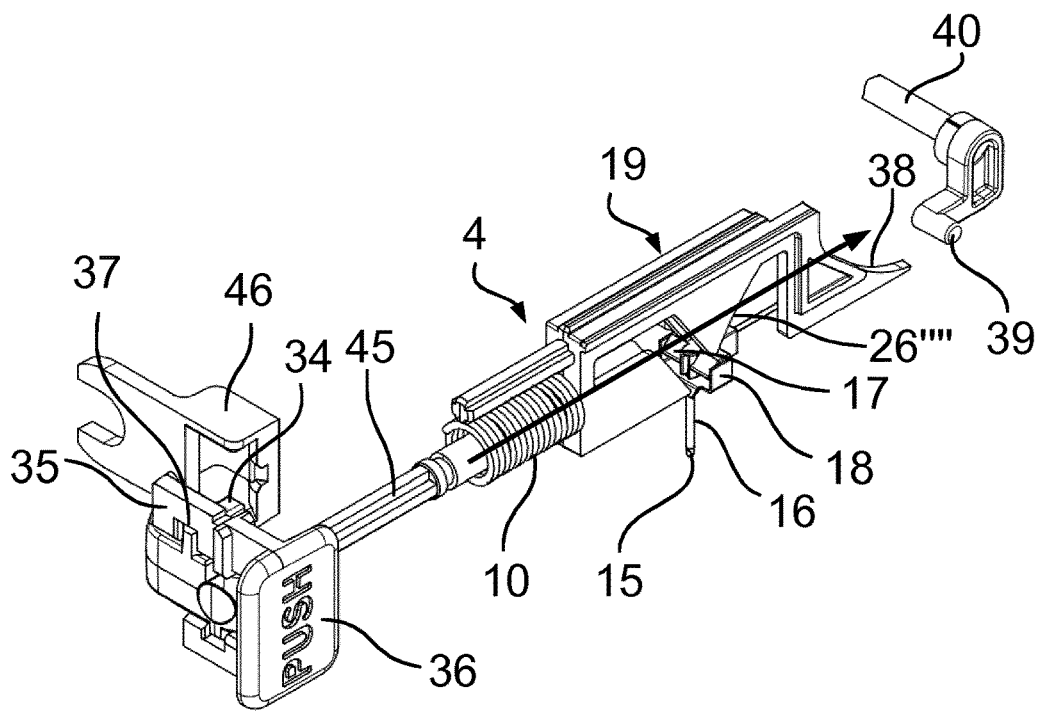

In FIG. 14, the control element 19 is already displaced (in the direction of the arrow) over the first part of the control range. By means of the surface 26'''', this has led to a simultaneous, co-directional displacement of the two runners 17, 18 and thus to placement of the indwelling cannula 16 with the aid of the puncture cannula 15.

It goes without saying that an expansion of the helical spring 20 occurs during the displacement of the control element 19. However, for technical drawing reasons, the spring is always shown in the compressed state in FIGS. 13 to 16.

Figure 15:
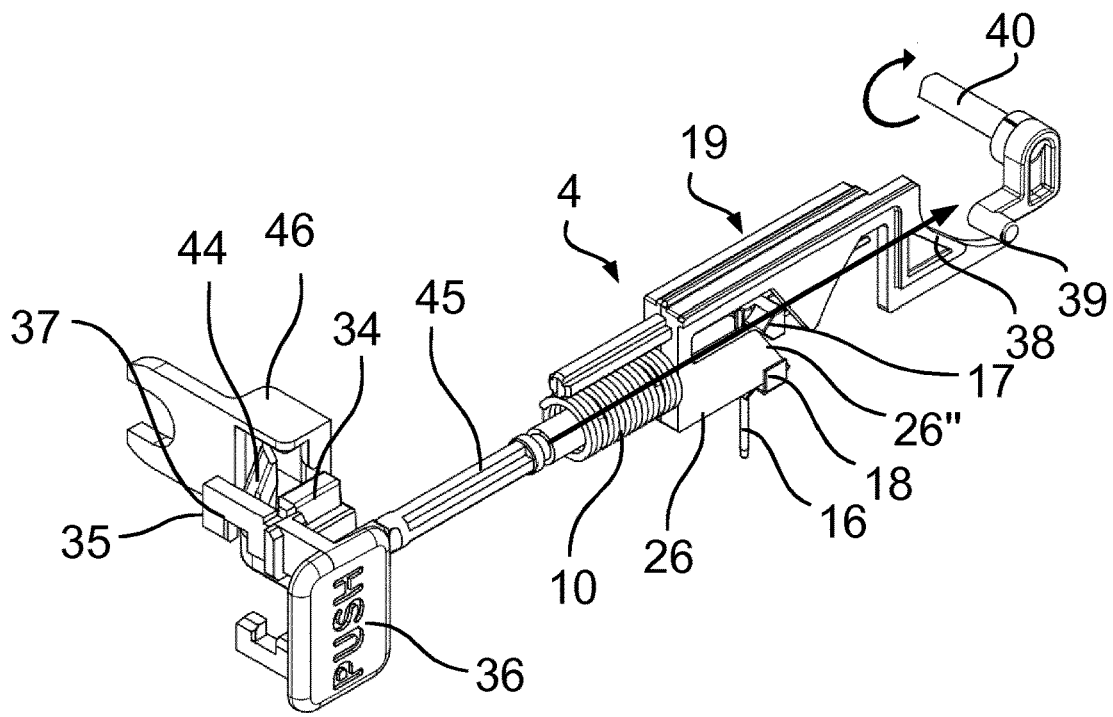

FIG. 15 shows the displacement of the control element 19 over a second part of the control range. On the one hand, a blocking of the second runner 18, designed as a holding plate, and hence a holding of the indwelling cannula 16 in the dwell position, is here obtained merely by acting on, especially pressing down, the control element 19 with the can surface 26. On the other hand, by means of the cam surface 26", a withdrawal of the puncture cannula 15 from the distal end region of the indwelling cannula 16 is obtained.

The control element 19 has an additional, cam surface 38 which, in the second part of the control range, acts on the lever element 39. The lever element 39 is thereby movable from the first position, shown in FIG. 15, to a second position, depicted in FIG. 16, resulting in a rotation of a pivot pin 40. The control element 19 can thus control further functions of a corresponding device, for instance a dosing appliance. Thus, a valve device or conveying device can be activated in order to conduct a fluid to the injection device. For example, a valve device can be switched such that the liquid is diverted by a transfer means 5 into the desired direction, namely from the first container 2 to the injection device.

Figure 16:
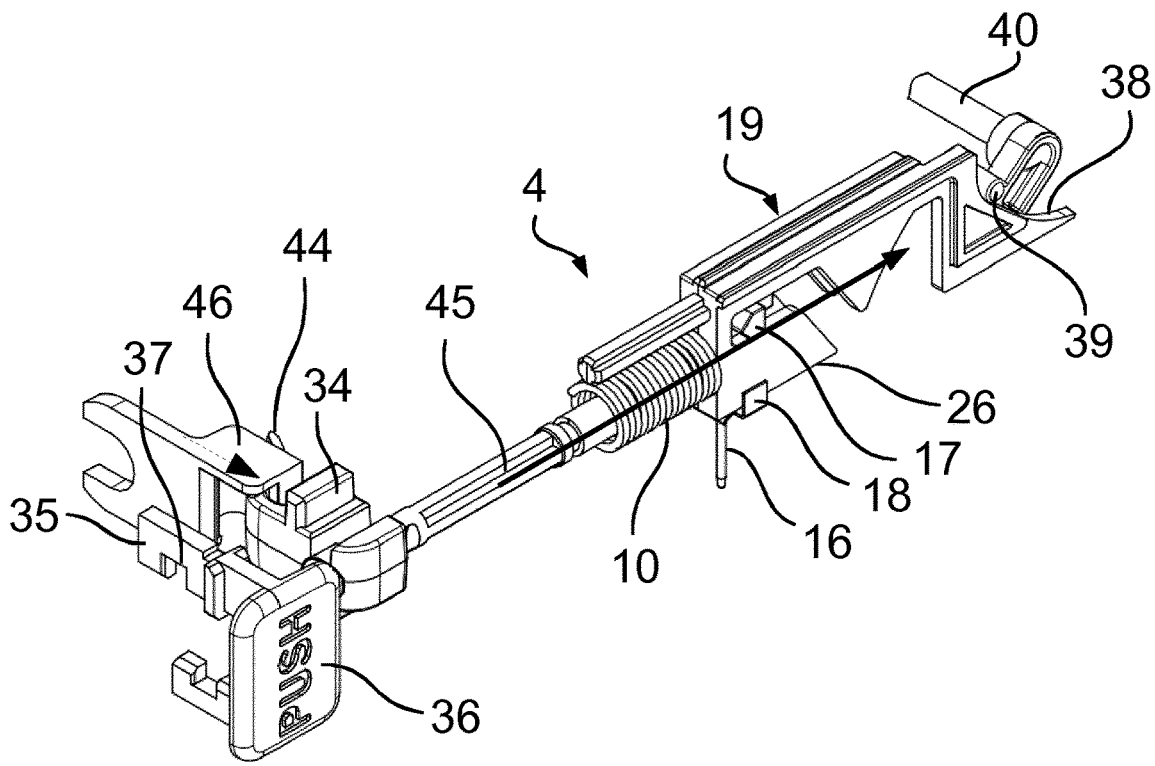

In the present illustrative embodiment, the injection device additionally has a further cam surface 44, which is not mounted directly on the control element 19. Said cam surface 44 is formed integrally with the stop element 34 and is connected to the control element 19 via a rod 45. When the pushbutton 36 is moved in the direction of the arrow shown in FIG. 13, the element 34 is displaced such that it passes through the aperture 37. In this way, the displacement of the control element 19 along the arrow shown in FIG. 14 is triggered. While the stop element 34 slides together with the control element in the direction of the arrow shown, it acts on the slide 46 and displaces it. The movement of the slide 46 can be seen in FIGS. 15 and 16. The sliding movement arises from the fact that the cam surface 44 engages through an aperture into the slide 46. The slide 46 is thereby transferred (dotted arrow) along a direction of displacement perpendicular to the direction of displacement of the control element 19. Alternatively, the slide can be displaced in an oblique direction that describes an angle between the dotted arrow and the solid arrow (FIG. 16).

Figure 17:
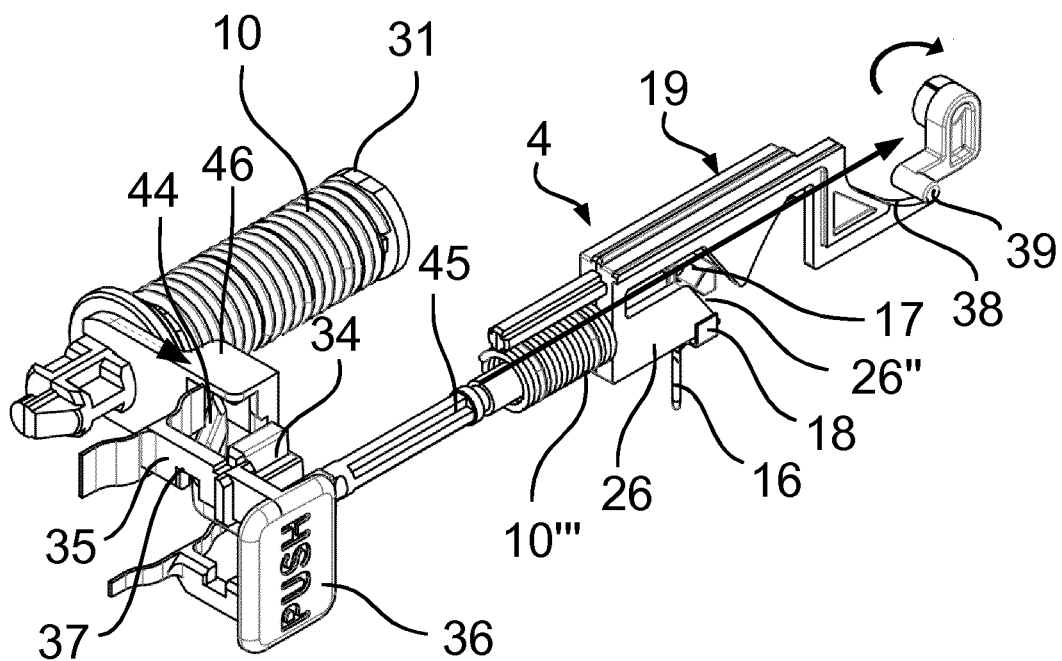

The state shown in FIG. 15 is shown once again in FIG. 17. However, in order to illustrate the function of the slide, the interaction of the latter with a piston rod 31 is indicated. The movement of the slide toward the control element is shown by the dotted arrow. The movement of the piston rod 31, which acts oil the piston 9 in the first container 2, is shown as a solid arrow. Through the release of the spring element 10, which was secured beforehand in a tensioned position by the slide 46, the sliding movement of the piston rod 31 is triggered, and therefore the injection. The displacement of the slide can take place simultaneously with the switching of the valve by lever 40 or can take place subsequent to the switching of the valve, in which case the time lag between the triggering processes is very short.

The invention claimed is:

1. A device for dispensing a substance to a patient comprising:
   a housing;
   a cylindrical first container containing the substance and a first piston;
   a second container containing a liquid and a second piston;
   an indwelling cannula;
   a transfer conduit for transferring the liquid from the second container to the first container and from the first container to the indwelling cannula, the first container having, at a first end, an attachment element, where the first piston is displaceable between the first end and a second end, so that, by displacement of the first piston toward the first end of the first container, a liquid contained in the first container can be dispensed via the indwelling cannula, wherein a puncture cannula is slidably positioned within the indwelling cannula, and, in a starting position, a distal end region of the puncture cannula extends coaxially in an interior of the indwelling cannula
   a valve in fluid communication with the transfer conduit, where the valve has a closed position and an open position, when the valve is in an open position the liquid contained in the first container can be dispensed via the indwelling cannula;
   a lever operatively connected to the valve;
   a first runner and a second runner, wherein the first runner is connected to the puncture cannula and the second runner is connected to the indwelling cannula;
   a control element operatively connected to the lever, to the first runner and to the second runner such that axial movement of the control element from an initial position to a final position directly causes,
      the first runner to move transversely relative to the movement of the control element in a penetrating direction and then in a reverse withdrawal direction,
      the second runner to move transversely relative to the movement of the control element in the penetrating direction and then to locked position, and
      the lever to move such that lever moves the valve from the closed position to the open position,
   wherein the first piston is operatively engaged with a first piston rod and the second piston is operative engaged with a second piston rod,
   wherein the first and second containers move axially from a first position to a second position when a retention element is disengaged from both the first and second piston rods, and
   wherein movement from the first position to the second position causes a penetration of septum on each of the first and second containers such that the first and second containers become in fluid communication with each other and with the transfer conduit.

2. The device according to claim 1, wherein the control element is pretensioned via a first spring element.

3. The device according to claim 2, wherein the control element is held back counter to the pretensioning via a retainer that is released by an activator.

4. The device according to claim 2, wherein a spring element for displacing the first piston is activatable via the activator.

5. The device according to claim 1, wherein the substance is a solid or a liquid.

6. The device according to claim 1, wherein the second container is likewise cylindrical, with an attachment element at a first end, and where the second piston is movable between the first end and a second end.

7. The device according to claim 6, wherein the second container is arranged parallel to the first container.

8. The device according to claim 1, wherein the first piston of the first container and the second piston of the second container are pretensioned and displaceable by a respective second spring element and a third spring element.

9. The device according to claim 1, wherein the first container can be brought into fluidic communication with the second container or the indwelling cannula via the valve.

10. The device according to claim 1, where the housing comprises an external contact face via which the device can be placed.

11. The device according to claim 10, wherein the puncture cannula and the indwelling cannula are arranged substantially inside the housing in the starting position and are deployed from the housing through an application opening in the contact face.

12. The device according to claim 1, wherein the control element is configured as a displaceable cam carrier.

13. The device according to claim 1, wherein the control element comprises a linearly displaceable carriage on which at least one cam carrier is formed.

14. The device according to claim 13, wherein the direction of displacement of the carriage runs parallel to longitudinal center axes of the first container and second container.

* * * * *